United States Patent [19]

Böttcher et al.

[11] Patent Number: 4,975,466

[45] Date of Patent: Dec. 4, 1990

[54] PHARMACEUTICAL PREPARATIONS FOR TOPICAL APPLICATION AND THEIR USE IN THE TREATMENT OF INFLAMMATORY SKIN DISEASES

[75] Inventors: Irmgard Böttcher, Basel; Werner Pignat, Windisch, both of Switzerland

[73] Assignee: Ciba-Geigy Corporation, Ardsley, N.Y.

[21] Appl. No.: 282,928

[22] Filed: Dec. 7, 1988

[30] Foreign Application Priority Data

Jun. 5, 1986 [CH]  Switzerland ................ 2290/86

[51] Int. Cl.$^5$ ............................................ A61K 31/16
[52] U.S. Cl. .................................. 514/630; 514/863; 514/887
[58] Field of Search .................. 514/630, 863, 887

[56] References Cited

U.S. PATENT DOCUMENTS

| | | | |
|---|---|---|---|
| 3,994,974 | 11/1976 | Murakami et al. | 260/562 A |
| 4,268,501 | 5/1981 | Konno et al. | 424/80 |
| 4,303,637 | 12/1981 | Shell et al. | 424/14 |
| 4,380,534 | 4/1983 | Fukui et al. | 424/38 |
| 4,685,911 | 8/1987 | Konno et al. | 604/897 |

FOREIGN PATENT DOCUMENTS

| | | |
|---|---|---|
| 2305092 | 8/1973 | Fed. Rep. of Germany . |
| 2401450 | 7/1974 | Fed. Rep. of Germany . |

OTHER PUBLICATIONS

Agents and Actions, vol. 19, p. 368 (1986).
Proceeding of the Society for Experimental Biology and Medicine, vol. 159, pp. 223–225 (1978).
British Journal of Dermatology, vol. 99, pp. 197–200 (1978).
Biochemical Society Transactions, vol. 14, pp. 388–391 (1986).
Derwent Abstract 40030w.
Arch. Int. Pharmacodyn, vol. 250, pp. 279–292 (1981).
CA 100: 61603 d (1984).
Allergy, vol. 38, pp. 547–552 (1983).

*Primary Examiner*—Leonard Schenkman
*Attorney, Agent, or Firm*—JoAnn Villamizar

[57] ABSTRACT

Pharmaceutical preparations for topical, i.e. dermal, application that contain as active ingredient a compound of the formula I

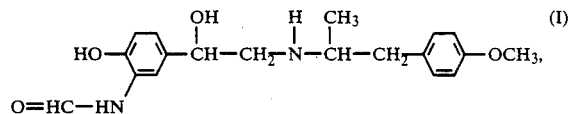

especially 2-hydroxy-5-[(RS)-1-hydroxy-2-[[(RS)-1-(p-methoxyphenyl)-prop-2-yl]-amino]-ethyl]-formanilide (formoterol), or one of its pharmaceutically acceptable salts, especially its semifumarate, are proposed for the treatment of inflammatory skin diseases.

15 Claims, No Drawings

PHARMACEUTICAL PREPARATIONS FOR TOPICAL APPLICATION AND THEIR USE IN THE TREATMENT OF INFLAMMATORY SKIN DISEASES

This application is a continuation of U.S. patent application Ser. No. 054,719, filed 05/27/87 abandoned.

The invention relates to novel pharmaceutical preparations for topical, i.e. dermal, application that contain as active ingredient a compound of the formula I

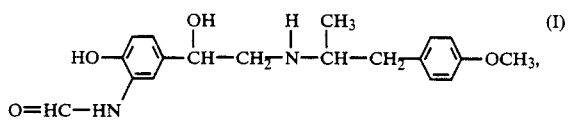

especially 2-hydroxy-5-[(RS)-1-hydroxy-2-[[(RS)-1-(p-methoxyphenyl)-prop2-yl]-amino]-ethyl]-formanilide (formoterol), or one of its pharmaceutically acceptable salts, especially its semifumarate, to processes for the manufacture of such pharmaceutical preparations and to the use of compounds of the formula I and their pharmaceutically acceptable salts. Pharmaceutically acceptable salts of a compound of the formula I are pharmaceutically acceptable acid addition salts, for example salts with inorganic acids, such as mineral acids, with sulphamic acids, such as cyclohexylsulphamic acid, with organic carboxylic acids, such as lower alkanecarboxylic acids or optionally unsaturated dicarboxylic acids, with aliphatic carboxylic acids substituted by hydroxy and/or by oxo, or with aliphatic or aromatic sulphonic acids, for example sulphates or hydrohalides, such as hydrobromides or hydrochlorides, oxalates, malonates, fumarates or maleates, tartrates, pyruvates or citrates and also sulphonates, such as methane-, benzene-or p-toluenesulphonates. There are to be understood by lower alkanecarboxylic acids preferably those containing up to and including 7, above all up to and including 4, carbon atoms (C-atoms) in the lower alkyl moiety.

The pharmaceutically acceptable salts of a compound of the formula I may also be in the form of its hydrates or may include other solvents being pharmaceutically safe, for example solvents used for crystallisation.

Owing to the close relationship between a compound of the formula I in free form and in the form of its pharmaceutically acceptable salts, hereinbefore and hereinafter there is to be understood by a free compound or its salts optionally also the corresponding salts or the free compound, respectively, where appropriate with regard to meaning and purpose. Accordingly, hereinafter there is to be understood by formoterol both the free base and its pharmaceutically acceptable salts, especially its semifumarate.

Formoterol and its pharmaceutically acceptable salts are known and are described, for example, in German Offenlegungsschrift DE-2 305 092 (Yamanouchi Pharmaceutical Co. Ltd., Tokyo).

As explained in that specification, formoterol and its pharmaceutically acceptable salts belong to the class of $\beta$-adrenergic stimulators and are stated to be suitable as bronchodilatory agents owing to their great activity on the non-striated respiratory musculature, oral and parenteral forms of administration being described.

In contrast, pharmaceutical preparations of compounds of the formula I and their pharmaceutically acceptable salts for topical, i.e. dermal, application to the skin and/or mucous membrane are new. There is no mention in this respect in the prior art.

Within the framework of the present invention, it has surprisingly been found that formoterol, in particular, has as an additional valuable pharmacological property when applied topically, i.e dermally, to the skin and/or mucous membrane a very pronounced antiphlogistic (dermally phlogistatic), that is to say topically anti-inflammatory, action Hereinbefore and hereinafter there are to be understood by pharmaceutical preparations for topical, i.e. dermal, application to the skin and/or mucous membrane dermatological pharmaceutical preparations for external use on the outer skin, including the conjunctiva of the eyeball, the lips and the genital and anal region.

The antiphlogistic action of formoterol and its pharmaceutically acceptable salts can be demonstrated using suitable animal models For example, tests with formoterol in the form of the free base in a concentration range of from approximately 0.03 to approximately 30 mg/ml on experimental aural oedema induced by croton oil in rats showed an inhibiting concentration $EC_{50}$ of approximately 0.5 mg/ml and, in a concentration range of from approximately 0.01 to approximately 10 mg/ml on experimental aural oedema induced by croton oil in mice, an inhibiting concentration $EC_{50}$ of approximately 0.32 mg/ml [methodology: in accordance with G. Tonelli et al., Endocrinology 77, 625 (1965)].

A very pronounced antiphlogistic action can also be detected in experimental aural oedema induced by arachidonic acid in mice. In this model, an inhibiting concentration EC50 of approximately 0.0026 mg/ml was found for formoterol in the form of the free base in a concentration range of from approximately 0.0005 to approximately 50 mg/ml [methodology: in accordance with J. M. Young et al., J. Invest. Dermatol 82, 367 (1984)].

Formoterol is therefore excellently suitable as a dermatological anti-phlogistic agent for the treatment of inflammatory dermatoses or proliferative dermatoses associated with inflammation, especially in the form of the topically administrable dermatological pharmaceutical preparations according to the invention. It can be used for a very wide variety of inflammatory dermatoses, especially those of an acute and sub-chronic kind, both of an allergic and of a non-allergic nature. Furthermore, formoterol is suitable for the treatment of proliferative skin diseases, especially those that are associated with inflammation, such as psoriasis, and can equally be used for the treatment of skin irritations, exanthemae and burns and for the treatment of inflammations of the conjunctiva of the eyeball, the lips and the genital and anal region.

The present invention relates also to a process for the treatment of inflammatory skin diseases of the kind described above, characterised by the topical, i.e. dermal, application of a compound of the formula I or one of its pharmaceutically acceptable salts.

The invention relates likewise to the use of a compound of the formula I or of one of its pharmaceutically acceptable salts for the treatment of inflammatory skin diseases of very different origins, especially for the treatment of dermatoses of the kind described above, and for the manufacture of the dermatological pharmaceutical preparations according to the invention.

The pharmaceutical preparations according to the invention which contain a compound of the formula I, especially formoterol, or pharmaceutically acceptable salts thereof are those for dermatological use in warm-blooded animals and contain the pharmacologically active ingredient on its own or together with a pharmaceutically acceptable carrier. The daily dosage of the active ingredient depends on the age and the individual condition and also on the mode of administration. Corresponding agents having an active ingredient content of from approximately 0.00001 to approximately 1% by weight, for example in the form of creams, ointments or solutions, may be applied, for example, 2 or 3 times daily.

Suitable dermatologically administrable pharmaceutical preparations are especially creams, ointments, fatty ointments, pastes, gels, foams, tinctures and solutions and, for the treatment of the conjunctiva of the eyeball, eye drops, each of which preparations contains, for example, from approximately 0.00001 to approximately 1% by weight, especially from approximately 0.0005 to approximately 0.5% by weight, active ingredient.

Creams are oil-in-water emulsions that contain more than 50% water. As oily base material there are used especially fatty alcohols, for example lauryl, cetyl or stearyl alcohol, fatty acids, for example palmitic or stearic acid, liquid to solid waxes, for example isopropyl myristate, wool wax or beeswax, and/or hydrocarbons, for example vaseline (petrolatum) or paraffin oil. Suitable emulsifiers are surface-active substances having predominantly hydrophilic properties, such as corresponding non-ionic emulsifiers, for example fatty acid esters of polyalcohols or ethylene oxide adducts thereof, such as polyglycerol fatty acid esters or polyoxyethylene sorbitan fatty acid esters (Tweens), also polyoxyethylene fatty alcohol ethers or fatty acid esters, or corresponding ionic emulsifiers, such as alkali metal salts of fatty alcohol sulphates, for example sodium lauryl sulphate, sodium cetyl sulphate or sodium stearyl sulphate, which are customarily used in the presence of fatty alcohols, for example cetyl alcohol or stearyl alcohol Additives to the aqueous phase are, inter alia, agents that reduce drying out of the creams, for example polyalcohols, such as glycerol, sorbitol, propylene glycol and/or polyethylene glycols, and also preservatives, perfumes, etc.

Ointments are water-in-oil emulsions that contain up to 70%, but preferably from approximately 20% to approximately 50%, water or aqueous phases. Suitable as fatty phase are especially hydrocarbons, for example vaseline, paraffin oil and/or hard paraffins, which preferably contain suitable hydroxy compounds, such as fatty alcohols or esters thereof, for example cetyl alcohol or wool wax alcohol or wool wax, in order to improve their capacity to bind water. Emulsifiers are corresponding lipophilic substances, such as sorbitan fatty acid esters (Spans), for example sorbitan oleate and/or sorbitan isostearate. Additives to the aqueous phase are, inter alia, moisture-retaining agents, such as polyalcohols, for example glycerol, propylene glycol, sorbitol and/or polyethylene glycol, and preservatives, perfumes, etc..

Fatty ointments are anhydrous and contain as base material especially hydrocarbons, for example paraffin, vaseline and/or liquid paraffins, and natural or partially synthetic fats, for example coconut fatty acid triglyceride, or preferably hardened oils, for example hydrogenated groundnut or castor oil, and fatty acid partial esters of glycerol, for example glycerol mono- or distearate, and also, for example, the fatty alcohols that increase the water absorption capacity and the emulsifiers and/or additives mentioned in connection with the ointments.

Pastes are creams and ointments with secretion-absorbing powder constituents, such as metal oxides, for example titanium oxide or zinc oxide, also talc and/or aluminium silicates, the function of which is to bind any moisture or secretions present.

In the case of gels, a distinction is made between aqueous and anhydrous or low-water-content gels which consist of swellable, gel-forming materials. There are used especially transparent hydrogels based on inorganic or organic macromolecules. High molecular weight inorganic components having gel-forming properties are predominantly water-containing silicates, such as aluminium silicates, for example betonite, magnesium aluminium silicate, for example veegum, or colloidal silica, for example aerosil. As high molecular weight organic substances there are used, for example, natural, semi-synthetic or synthetic macromolecules. Natural and semi-synthetic polymers are derived, for example, from polysaccharides having very varied carbohydrate building blocks, such as celluloses, starches, tragacanth, gum arabic, agar-agar, gelatine, alginic acid and salts thereof, for example sodium alginate, and derivatives thereof, such as lower alkylcelluloses, for example methyl- or ethyl-celluloses, and carboxy-or hydroxy lower alkylcelluloses, for example carboxymethyl-or hydroxyethyl-celluloses. The building blocks of synthetic, gel-forming macromolecules are, for example, correspondingly substituted unsaturated aliphatic compounds, such as vinyl alcohol, vinylpyrrolidine, acrylic acid or methacrylic acid. As examples of such polymers there may be mentioned polyvinyl alcohol derivatives, such as polyviol, polyvinylpyrrolidines, such as collidine, polyacrylates and polymethacrylates, such as Rohagit S or Eudispert. Customary additives, such as preservatives or perfumes, may be added to the gels.

Foams are administered, for example, from pressurised containers and are oil-in-water emulsions in aerosol form, there being used as propellants halogenated hydrocarbons, such as chlorofluoro-lower alkanes, for example dichlorodifluoromethane or dichlorotetrafluoroethane. As oily phase there are used, *inter alia*, hydrocarbons, for example paraffin oil, fatty alcohols, for example cetyl alcohol, fatty acid esters, for example isopropylmyristate, and/or other waxes. As emulsifiers there are used, *inter alia*, mixtures of those having predominantly hydrophilic properties, such as polyoxyethylene sorbitan fatty acid esters (Tweens), and those having predominantly lipophilic properties, such as sorbitan fatty acid esters (Spans). The customary additives, such as preservatives, etc. are added thereto.

Tinctures and solutions have in most cases an aqueous-ethanolic base to which have been added, *inter alia*, polyalcohols, for example glycerol, glycols and/or polyethylene glycol, as moisture-retaining agents to reduce evaporation and fat-restoring substances, such as fatty acid esters with low molecular weight polyethylene glycols, that is to say lipophilic substances that are soluble in aqueous mixture as a replacement for the fatty substances removed from the skin with the ethanol, and, if necessary, other adjuncts and additives.

Eye drops are usually sterile aqueous solutions that have been adjusted to the physiological pH range of from 6 to 8. The concentration of the buffers, such as phosphate or acetate buffers, used, for example, to adjust the pH is so selected that the pH value of the lachrymal fluid is not affected for a prolonged period thereby causing pain. The isotonicity with the lachrymal fluid is obtained mostly by the addition of salts, such as sodium citrate or preferably sodium chloride, or mannitol. In addition, the customary adjuncts, for example anti-oxidants, such as sodium pyrosulphite, preservatives, such as benzalkonium chloride, cetylpyridinium chloride or 2-phenylethyl alcohol, and optionally solution aids, for example polyoxyethylene sorbitan monooleate, polyoxyethylene glycol or α-or β-cyclodextrin, are added The dermatologically administrable pharmaceutical preparations are prepared in a manner known per se by mixing with pharmaceutical adjuncts that are customary for that purpose, for example by dissolving or suspending the active ingredient in the base material or in a portion thereof, if necessary In order to prepare emulsions in which the active ingredient is dissolved in one of the liquid phases, the active ingredient is, as a rule, dissolved therein before the emulsification; in order to prepare suspensions in which the active ingredient is suspended in the emulsion, the active ingredient is mixed with a portion of the base material after the emulsification and then added to the remainder of the formulation.

The following Examples illustrate the invention described above but are not intended to limit the scope thereof in any way. Temperatures are given in degrees Celsius.

EXAMPLE 1

An ointment containing 0.05% 2-hydroxy5-[(RS)-1-hydroxy-2-[[(RS)-1-(p-methoxyphenyl)-prop2-yl]-amino]-ethyl]-formanilide or its semifumarate can be prepared as follows:

| Composition | |
|---|---|
| active ingredient | 0.05% |
| vaseline | 45.00% |
| paraffin oil | 19.60% |
| cetyl alcohol | 5.00% |
| beeswax | 5.00% |
| sorbitan sesquioleate | 5.00% |
| p-hydroxybenzoic acid ester | 0.20% |
| water, demineralised, up to | 100.00% |

The fatty substances and emulsifiers are melted together. The preservative is dissolved in water, and the solution is emulsified in the fatty melt at elevated temperature. After cooling, a suspension of the active ingredient in a portion of the fatty melt is incorporated into the emulsion

EXAMPLE 2

A cream containing 0.5% 2-hydroxy-5-[(RS)-1- hydroxy-2-[[(RS)-1-(p-methoxy-phenyl)-prop-2-yl]- amin o]-ethyl]-formanilide or its semifumarate can be prepared as follows:

| Composition | |
|---|---|
| active ingredient | 0.5% |
| isopropyl palmitate | 8.0% |
| cetyl palmitate | 1.5% |
| silicone oil 100 | 0.5% |
| sorbitan monostearate | 3.0% |
| polysorbate 60 | 3.5% |
| 1,2-propylene glycol PH | 20.0% |
| acrylic acid polymer | 0.5% |
| triethanolamine | 0.7% |
| water, demineralised, up to | 100.0% |

The acrylic acid polymer is suspended in a mixture of demineralised water and 1,2-propylene glycol. While stirring, triethanolamine is then added which produces a slime. A mixture of isopropyl palmitate, cetyl palmitate, silicone oil, sorbitan monostearate and polysorbate is heated to approximately 75° and, while stirring, is incorporated into the slime which has likewise been heated to approximately 75°. Having cooled to room temperature, the cream base material is then used to prepare a concentrate with the active ingredient. The concentrate is homogenised by means of a continuous homogeniser and then added in portions to the base material.

EXAMPLE 3:

A cream containing 0.05% 2-hydroxy-5-[(RS)-1-hydroxy-2-[[(RS)-1-(p-methoxyphenyl)-prop-2-yl]-amino]-ethyl]-formanilide or its semifumarate can be obtained as follows:

| Composition | |
|---|---|
| active ingredient | 0.05% |
| cetyl palmitate PH | 2.00% |
| cetyl alcohol PH | 2.00% |
| triglyceride mixture of saturated medium-fatty fatty acids | 5.00% |
| stearic acid | 3.00% |
| glycerol stearate PH | 4.00% |
| cetomacrogol 1000 | 1.00% |
| microcrystalline cellulose | 0.50% |
| 1,2-propylene glycol, distilled | 20.00% |
| water, demineralised, up to | 100.00% |

Cetyl alcohol, cetyl palmitate, the triglyceride mixture, stearic acid and glycerol stearate are melted together. The microcrystalline cellulose is dispersed in a portion of the water. Cetomacrogol is dissolved in the remainder of the water. Cetomacrogol is dissolved in the remainder of the water, and the propylene glycol and the slime are mixed therewith. The fatty phase is then added to the aqueous phase while stirring and the whole is stirred until cool. Finally, the active ingredient is rubbed into a portion of the base material and then incorporated by rubbing into the remainder of the cream.

EXAMPLE 4

A transparent hydrogel containing 0.5% 2-1-hydroxy-5-[(RS)-1-hydroxy-2-[[(RS)-1-(p-methoxyphenyl)-prop-2-yl]-amino]-ethyl]-formanilide or its semifumarate is prepared as follows:

| Composition | |
|---|---|
| active ingredient | 0.5% |
| propylene glycol | 10.0-20.0% |
| isopropanol | 20.0% |
| hydroxypropylmethylcellulose | 2.0% |
| water | up to 100.0% |

The hydroxypropylmethylcellulose is swelled in water. The active ingredient is dissolved in a mixture of isopropanol and propylene glycol. The active ingredient solution is then mixed with a swelled cellulose derivative and, if desired, perfumes (0.1%) are added thereto.

EXAMPLE 5

A transparent hydrogel containing 0.005% 2-hydroxy-5-[(RS)-1-hydroxy-2-[[(RS)-1-(p-methoxyphenyl)-prop-2-yl]-amino]-ethyl]-formanilide or its semifumarate is prepared as follows:

| Composition | |
|---|---|
| active ingredient | 0.005% |
| propylene glycol | 20.0% |
| isopropanol | 20.0% |
| acrylic acid polymer | 2.0% |
| triethanolamine | 3.0% |
| water | up to 100.0% |

Acrylic acid polymer and water are dispersed and neutralised with triethanolamine. The active ingredient is dissolved in a mixture of isopropanol and propylene glycol. The active ingredient solution is then mixed with the gel and, if desired, perfume (0.1%) can be added.

EXAMPLE 6

A foam spray containing 0.01% 2-hydroxy-5-[(RS)-1-hydroxy-2-[[(RS)-1-(p-methoxy-phenyl)-prop-2-yl]-amino]-ethyl]-formanilide or its semifumarate can be prepared as follows.

| Composition: | |
|---|---|
| active ingredient | 0.01% |
| cetyl alcohol PH | 1.70% |
| paraffin oil, viscous | 1.00% |
| isopropyl myristate | 2.00% |
| cetomacrogol 1000 | 2.40% |
| sorbitan monostearate | 1.50% |
| 1,2-propylene glycol PH | 5.00% |
| methylparaben | 0.18% |
| propylparaben | 0.02% |
| chemoderm 314 | 0.10% |
| water, demineralised, | up to 100.00% |

Cetyl alcohol, paraffin oil, isopropyl myristate, cetomacrogol and sorbitan stearate are melted together. Methyl- and propyl-paraben are dissolved in hot water. The melt and the solution are then mixed. The active ingredient, suspended in propylene glycol, is incorporated into the base material Chemoderm is then introduced and water is added until the final weight is obtained.

Introduction into containers 20 ml of the mixture are introduced into an aluminium block can. The can is provided with a valve and the propellant gas is introduced under pressure.

EXAMPLE 7

Eye drops containing 0.3% 2-hydroxy-5-[(RS)-1-hydroxy-2-[[(RS)-1-(p-methoxyphenyl)-prop2-yl]-amino]-ethyl-formanilide or its semifumarate can be prepared as follows:

| Composition (for 10,000 bottles each containing 10 ml of eye drop solution): | |
|---|---|
| active ingredient | 0.30% |
| disodium phosphate | 0.31% |
| citric acid | 0.15% |
| sodium chloride | 0.35% |
| sodium pyrosulphite | 0.10% |
| benzalkonium chloride | 0.01% |
| water, demineralised, | up to 100.00% |

The active ingredient and all the additives mentioned are stirred into 80 litres of demineralised water under a nitrogen atmosphere. When all the ingredients have dissolved completely, the solution is made up to 100 litres with demineralised water, sterilised in an autoclave at 120° for 20 minutes and then filtered under sterile conditions through a membrane filter (pore diameter: 0.2 μm). Every 10 ml of the filtrate is introduced under aseptic conditions into a bottle having a dropping pipette closure.

EXAMPLE 8

Dermatologically administrable pharmaceutical preparations that contain a different pharmaceutically acceptable salt of formoterol can also be prepared in a manner analogous to that described in Examples 1 top 7.

EXAMPLE 9

Dermatologically administrable pharmaceutical preparations that contain a different compound of the formula I or a pharmaceutically acceptable salt thereof can also be prepared in a manner analogous to that described in Examples 1 to 7.

We claim:

1. A topical anti-inflammatory pharmaceutical preparation comprising a topical anti-inflammatory effective amount of a compound of the formula

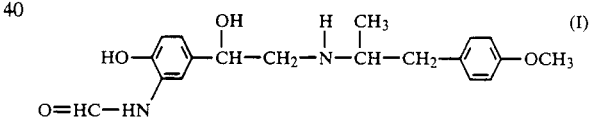

or a pharmaceutically acceptable salt thereof together with a pharmaceutically acceptable carrier, said preparation being selected from the group consisting of a gel, a foam, a tincture comprising an aqueous-ethanolic solution and a fat restoring substance as a replacement for fatty substances removed from the skin by ethanol, and an eye drop having a pH of from 6 to 8 and being isotonic with lachrymal fluid.

2. The topical anti-inflammatory pharmaceutical preparation of claim 1 wherein said gel is selected from the group consisting of hydrogels, low-water content gels and anhydrous gels of swellable gel-forming material; said foam is an oil-in-water emulsion in aerosol foam; said tincture comprises an aqueous-ethanolic solution and a fat restoring substance as a replacement for fatty substances removed from the skin by ethanol and said eye drop has a pH of from 6 to 8 and is isotonic with lachrymal fluid.

3. The preparation of claim 1 which is an eye drop.

4. The preparation of claim 1 wherein said compound of formula I is 2-hydroxy-5-[(RS)-1-hydroxy-2-[(RS)-1-(p-methoxyphenyl)-prop-2-yl]-amino]-ethyl]formanilide or a pharmaceutically acceptable salt thereof.

5. The preparation of claim 1 wherein said compound of formula I or a pharmaceutically acceptable salt thereof is 2-hydroxy-5-[(RS)-1-hydroxy-2-[[(RS)-1-hydroxy-2-[[(RS)-1-(p-methoxyphenyl)-prop-2-yl]-amino]-ethyl]-formanilide or the semifumarate salt thereof.

6. The pharmaceutical preparation of claim 1 wherein said compound of formula I or a pharmaceutically acceptable salt thereof is present in an amount of from about $1 \times 10^{-5}\%$ to about 1% by weight of said preparation.

7. The preparation of claim 1 wherein said compound of formula I or pharmaceutically acceptable salt thereof is present in an amount of from about $5 \times 10^{-4}\%$ to about 0.5% by weight of said preparation.

8. The preparation of claim 1 wherein said compound of formula I or a pharmaceutically acceptable salt thereof is the semifumarate salt of 2-hydroxy-5-[(RS)-1-(p-methoxyphenyl)-prop-2-yl]-amino]ethyl]-formanilide.

9. The preparation of claim 1 which is a gel or an eye drop.

10. A method of treating an inflammatory skin disease in a warm-blooded animal in need thereof comprising topically administering to said warm-blooded animal a topical anti-inflammatory effective amount of a compound of the formula

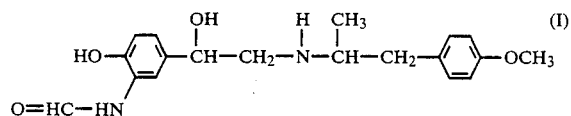

or a pharmaceutically acceptable salt thereof.

11. The method of claim 10 wherein said compound of formula I is 2-hydroxy-5-](RS)-1hydroxy-2-[[(RS)-1(p-methoxyphenyl)prop-2-yl]-amino]-ethyl]-formanilide or a pharmaceutically acceptable salt thereof.

12. The method of claim 10 wherein said compound of formula I or pharmaceutically acceptable salt thereof is 2-hydroxy-5-[(RS)-1-hydroxy-2-[[(RS)-1(P-methoxyphenyl)-prop--yl]-amino]-ethyl]-formanilide or the semifumarate salt thereof.

13. The method of claim 10 wherein said compound of formula I or a pharmaceutically acceptable salt thereof is the semifumarate salt of 2-hydroxy-5-[(RS)-1-hydroxy-2-[[(RS)-1-(p-methoxyphenyl)prop-2 -yl]-amino]-ethyl]-formanilide.

14. A method of treating an inflammatory skin disease in a warm-blooded animal in need thereof comprising topically administering to said warm-blooded animal a topical anti-inflammatory effective amount of a topical anti-inflammatory pharmaceutical preparation comprising from about $1 \times 10^{-5}\%$ to about 1% by weight of said preparation of a compound of the formula (1)

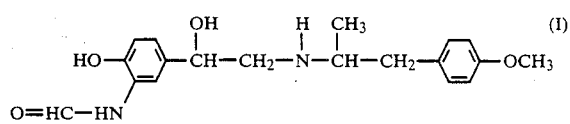

or a pharmaceutically acceptable salt thereof together with a pharmaceutically acceptable carrier, said preparation being selected from the group consisting of a cream, a paste, a gel, a foam, a tincture comprising an aqueous-ethanolic solution and a fat restoring substance as a replacement for fatty substances removed from the skin by ethanol, and an eye drop having a pH of from 6 to 8 and being isotonic with lachrymal fluid.

15. A method of treating an inflammatory skin disease according to claim 14 wherein said compound of formula (I) or a pharmaceutically acceptable salt thereof is present in an amount of from about $5 \times 10^4\%$ to about 0.5% by weight of said preparation.

* * * * *